(12) United States Patent
Wang et al.

(10) Patent No.: US 10,859,589 B2
(45) Date of Patent: Dec. 8, 2020

(54) FULL-AUTOMATIC BIOCHEMICAL ANALYZER, AND SAMPLING DEVICE AND SAMPLING METHOD THEREOF

(71) Applicant: LEADWAY (HK) LIMITED, Hong Kong (CN)

(72) Inventors: Bo Wang, Zhejiang (CN); Cheng Luo, Zhejiang (CN)

(73) Assignee: LEADWAY (HK) LIMITED, Hong Kong (CN)

(*) Notice: Subject to any disclaimer, the term of this patent is extended or adjusted under 35 U.S.C. 154(b) by 721 days.

(21) Appl. No.: 15/523,304

(22) PCT Filed: Dec. 15, 2014

(86) PCT No.: PCT/CN2014/093845
§ 371 (c)(1),
(2) Date: Apr. 28, 2017

(87) PCT Pub. No.: WO2016/065702
PCT Pub. Date: May 6, 2016

(65) Prior Publication Data
US 2017/0328927 A1    Nov. 16, 2017

(30) Foreign Application Priority Data
Oct. 28, 2014    (CN) .................... 2014 2 0629245 U

(51) Int. Cl.
*G01N 35/10*    (2006.01)
*G01N 35/00*    (2006.01)
(Continued)

(52) U.S. Cl.
CPC ............. *G01N 35/10* (2013.01); *G01N 35/00* (2013.01); *G01N 35/025* (2013.01); *G06F 19/34* (2013.01);
(Continued)

(58) Field of Classification Search
CPC ................ G01N 35/00; G01N 35/10; G01N 2035/00534; G01N 2035/0094; G01N 35/025; G06F 19/34
See application file for complete search history.

(56) References Cited

U.S. PATENT DOCUMENTS

2013/0017535 A1*  1/2013  Frey .................. G01N 35/10
                                                                435/5
2016/0289665 A1*  10/2016  Mao .................. C12M 47/06

FOREIGN PATENT DOCUMENTS

CN          2582256 Y    10/2003
CN          2857015 Y     1/2007
(Continued)

OTHER PUBLICATIONS

International Search Report and Written Opinion issued in WO 2016065702 (PCT/CN2014/093845) dated Jul. 21, 2015—incl Engl lang transl (20 pages total).
(Continued)

*Primary Examiner* — Shogo Sasaki
(74) *Attorney, Agent, or Firm* — Acuity Law Group, PC; Michael A. Whittaker

(57) ABSTRACT

The present invention provides an auto biochemical analyzer and a sampling device and a sampling method thereof. The auto biochemical analyzer comprises a frame (100), a horizontal motion system, a vertical motion system, a sampling component and a transfer guide track (101), wherein the horizontal motion system comprises a first stepping motor (116); the vertical motion system comprises a second stepping motor (103); the first stepping motor (116) and the second stepping motor (103) are fixedly installed on the frame (100) respectively; the sampling component comprises a sampling needle holder block (114) and a sampling needle (111); and the stepping motors (116, 103) are both fixed to the frame. The analyzer is smart in motion, low in (Continued)

cost and compact in structure, and has the functions of open sampling and closed puncturing as well as conveying a sample to a specific position.

5 Claims, 10 Drawing Sheets

(51) Int. Cl.
    *G01N 35/02*     (2006.01)
    *G06F 19/00*     (2018.01)

(52) U.S. Cl.
    CPC ............... *G01N 2035/0094* (2013.01); *G01N 2035/00534* (2013.01)

(56) References Cited

FOREIGN PATENT DOCUMENTS

| | | |
|---|---|---|
| CN | 201929963 U | 8/2011 |
| CN | 203249958 U | 10/2013 |
| CN | 203385745 U | 1/2014 |
| CN | 204269660 U | 4/2015 |
| CN | 204269661 U | 4/2015 |
| CN | 204269662 U | 4/2015 |
| CN | 104374933 B | 3/2016 |
| CN | 104374934 B | 8/2016 |
| CN | 104374935 B | 8/2016 |
| JP | 2000146775 A | 5/2000 |

OTHER PUBLICATIONS

International Preliminary Report on Patentability issued in WO 2016065702 (PCT/CN2014/093845) dated May 2, 2017—incl Engl lang transl (18 pages total).
Extended European Search Report and Written Opinion issued in EP 14904731 dated Jun. 13, 2018 (4 pages).
Response to Extended European Search Report and Written Opinion issued in EP 14904731 dated Jan. 3, 2019 (4 pages).
Office Action issued by SIPO in Chinese Patent Application No. 201410585159.4 dated Jul. 29, 2015 (10 pages total)—incl Engl lang transl.
Office Action issued by SIPO in Chinese Patent Application No. 201410586122.3 dated Jul. 29, 2015 (10 pages total)—incl Engl lang transl.
Office Action issued by SIPO in Chinese Patent Application No. 201410586215.6 dated Jul. 27, 2015 (10 pages total)—incl Engl lang transl.
Office Action issued by EPO in European Patent Application No. 14904731.8 dated Oct. 18, 2019.

* cited by examiner

FULL-AUTOMATIC BIOCHEMICAL ANALYZER, AND SAMPLING DEVICE AND SAMPLING METHOD THEREOF

CROSS-REFERENCE TO RELATED MATTERS

The present invention is filed under 35 U.S.C. § 371 as the U.S. national phase of International Patent Application No. PCT/CN2014/093845, filed Dec. 15, 2014, which designated the United States and claims priority to Chinese Patent Application No. 201420629245.6, filed Oct. 28, 2014, each of which is hereby incorporated in its entirety including all tables, figures and claims.

FIELD OF THE INVENTION

The present invention relates to an auto biochemical analyzer, and in particular to an auto blood cell analyzer for hematology analysis; and the present invention further relates to a sampling device and a sampling method of an auto biochemical analyzer. The sampling device can be applied to an auto hematology analyzer (auto blood cell analyzer) in the medical device industry, and has the functions of open sampling, closed sampling, sample transmission, etc.

BACKGROUND OF THE INVENTION

An auto biochemical analyzer is an instrument which is widely used in testing of physiological, chemical and physical properties of body fluid. A sampling device is a very important part in the auto biochemical analyzer. The sampling device needs to transport a liquid sample from a specimen bottle into a reagent bottle, and transport mixed liquid into a counter for detection after full reaction. The Chinese utility model patent 200520094284.1 discloses a sampling and stirring device of an auto biochemical analyzer. The device comprises a cantilever mechanism and a driving mechanism, the cantilever mechanism being connected to the driving mechanism. The cantilever mechanism comprises a sampling and stirring arm, a stirring paddle and a sampling needle, one end of the sampling and stirring arm being connected with the driving mechanism, and the other end being a free end. A motor is fixedly connected to the sampling and stirring arm by a motor bracket. A first bearing seat is fixedly connected below the free end of the sampling and stirring arm, a first rolling bearing being arranged therein, and a transmission shaft is installed on the first rolling bearing. Belt wheels are arranged on the motor and at one end of the transmission shaft, and the two belt wheels are connected by a transmission belt. The other end of the transmission shaft is fixedly connected with the stirring paddle. One end of the sampling needle is fixedly connected above the free end of the sampling and stirring arm through a sampling needle bracket, and the other end is inserted in the transmission shaft and the stirring paddle.

The above-mentioned auto biochemical analyzer comprises a rotating cantilever, so it can only rotate about its upright column within a limited angle, its motion range being limited, and thus the auto biochemical analyzer is not suitable for some occasions requiring two-dimensional freedom degree motion in a certain plane.

SUMMARY OF THE INVENTION

To overcome the shortcomings in the above-mentioned prior art, a first objective of the present invention is to provide a sampling device having a two-dimensional freedom degree motion function. The sampling device comprises: a frame, a horizontal motion system, a vertical motion system, a sampling component and a transfer guide track, wherein the horizontal motion system comprises a first stepping motor; the vertical motion system comprises a second stepping motor; the first stepping motor and the second stepping motor are fixedly installed on the frame respectively; the sampling component comprises a sampling needle holder block and a sampling needle; the transfer guide track is horizontally placed and is fixedly connected with the vertical motion system and the sampling needle holder block respectively; the horizontal motion system drives the sampling needle to move in the horizontal direction; and the vertical motion system drives the sampling needle to move in the vertical direction.

Further improvement of the above-mentioned technical solution is as follows: the horizontal motion system further comprises a first synchronous belt and a horizontal guide track; the vertical motion system further comprises a second synchronous belt, a first guiding shaft and a guide track holder block, the guide track holder block being fixedly connected with the second synchronous belt; and the sampling component further comprises a sampling component bracket and a second guiding shaft.

Further improvement of the above-mentioned technical solution is as follows: the sampling component bracket is fixedly connected with the first synchronous belt, and the sampling component bracket is fixed to a sliding block of the horizontal guide track; under the drive of the first stepping motor, the sampling component moves in the horizontal direction under the guide of the horizontal guide track; and the sliding block of the transfer guide track is fixedly connected with the sampling needle holder block, and the sampling needle holder block moves in the vertical direction with the transfer guide track under the drive of the second stepping motor.

Further improvement of the above-mentioned technical solution is as follows: the guide track holder block is fixedly connected with the transfer guide track.

Further improvement of the above-mentioned technical solution is as follows: the sampling needle holder block comprises a guiding column, and the guide track holder block is provided with a hole matched with the guiding column.

Further improvement of the above-mentioned technical solution is as follows: the guiding column is a partial cone.

Further improvement of the above-mentioned technical solution is further comprising an optocoupler switch, which is installed on the frame.

Further improvement of the above-mentioned technical solution is as follows: optocoupler switch sensor chips are respectively installed on the sampling component bracket and the guide track holder block.

Further improvement of the above-mentioned technical solution is as follows: the said transfer guide track and the horizontal guide track are parallel to each other.

Further improvement of the above-mentioned technical solution is as follows: the sampling component sequentially moves to a sampling position, a reaction cell position and a counting cell position in the horizontal direction.

A second objective of the present invention is to provide a sampling method using a sampling device, the sampling device comprising a frame, a horizontal motion system, a vertical motion system, a sampling component and a transfer guide track, wherein the horizontal motion system comprises a first stepping motor; the vertical motion system comprises a second stepping motor; the first stepping motor and the second stepping motor are installed on the frame respectively; the sampling component comprises a sampling needle holder block and a sampling needle; and the transfer guide track is horizontally placed and is fixedly connected with the vertical motion system and the sampling needle holder block respectively, the method comprising the following steps:

a) starting the first stepping motor to drive the sampling component to move to a sampling position in the horizontal direction, and turning off the first stepping motor;

b) starting the second stepping motor to drive the sampling needle to move in the vertical direction and penetrate through a container containing a sample, and return to the sampling position after aspirating the sample, and turning off the second stepping motor;

c) starting the first stepping motor to drive the sampling component to move to a reaction cell position in the horizontal direction, and turning off the first stepping motor;

d) starting the second motor to drive the sampling needle to move in the vertical direction and inject the sample into a reaction cell, and after a preset reaction time, to drive the sampling needle to aspirate part of mixed liquid after reaction and move to the reaction cell position, and turning off the second motor;

e) starting the first motor to drive the sampling needle to move to a counting cell position in the horizontal direction, and turning off the first motor;

f) starting the second motor to drive the sampling needle to move in the vertical direction and inject the part of the mixed liquid after reaction aspirated by the sampling needle into a counting cell and to drive the sampling needle to return to the counting cell position, and turning off the second motor; and g) starting the first motor to drive the sampling needle to move to an initial position in the horizontal direction, and turning off the first motor.

Further improvement of the above-mentioned technical solution is as follows: the horizontal motion system further comprises a first synchronous belt and a horizontal guide track; the vertical motion system further comprises a second synchronous belt, a first guiding shaft and a guide track holder block, the guide track holder block being fixedly connected with the second synchronous belt; and the sampling component further comprises a sampling component bracket and a second guiding shaft.

Further improvement of the above-mentioned technical solution is as follows: a first synchronous belt wheel is installed on a rotating shaft of the first stepping motor; the first synchronous belt moves in the horizontal direction under the drive of the first synchronous belt wheel; the sampling component bracket is fixedly connected with the first synchronous belt; the sampling component bracket is fixedly connected with a sliding block of the transfer guide track; the sliding block of the transfer guide track is fixedly connected with the sampling needle holder block; the transfer guide track and the horizontal guide track are placed in parallel; and when the first synchronous belt moves in the horizontal direction, the sampling component performs horizontal reciprocating motion under the guide of both the horizontal guide track and the transfer guide track.

Further improvement of the above-mentioned technical solution is as follows: the guide track holder block and the sampling needle holder block vertically slide on the first guiding shaft and the second guiding shaft respectively; the guide track holder block is fixedly connected with the synchronous belt; the sliding block of the transfer guide track is fixedly connected with the sampling needle holder block; when the second synchronous belt moves in the vertical direction under the drive of the second stepping motor, the guide track holder block indirectly drives, through the transfer guide track, the sampling needle holder block to perform vertical reciprocating motion under the guide of the first guiding shaft and the second guiding shaft; and the sampling needle is fixedly connected with the sampling needle holder block, and the sampling needle performs vertical lifting motion with the transfer guide track under the drive of the second synchronous belt so as to accomplish a sample aspirating action and a sample conveying action.

Further improvement of the above-mentioned technical solution is as follows: when the second stepping motor is turned off and the first stepping motor is turned on, the sampling component moves to a specified position in the horizontal direction; and when the first stepping motor is turned off and the second stepping motor is turned on, the sampling needle performs the vertical lifting motion with the transfer guide track under the drive of the second synchronous belt.

Further improvement of the above-mentioned technical solution is as follows: the specified position comprises the sampling position, the reaction cell position and the counting cell position.

Further improvement of the above-mentioned technical solution is as follows: the sampling device further comprises an optocoupler switch, which is installed on the frame; and optocoupler switch sensor chips are respectively installed on the sampling component bracket and the guide track holder block, and when the sensor chips shield the optocoupler, a switching signal is sent to a control system.

Further improvement of the above-mentioned technical solution is as follows: the sampling needle holder block comprises a guiding column, and a conical hole matched with the guiding column is formed in a corresponding position of the guide track holder block, and when the sampling component is in contact with the guide track holder block, the guiding column is screwed into the conical hole to keep close contact between the sampling component and the holder block.

Further improvement of the above-mentioned technical solution is as follows: the guiding column is a cone.

Further improvement of the above-mentioned technical solution is as follows: when the sampling component moves into contact with the guide track holder block in the horizontal direction, the sampling needle holder block combines with the guide track holder block through the guiding column and the conical hole, and then the sampling needle holder block, together with the guide track holder block, drives the sampling needle to execute tube puncturing and sample aspirating actions under the traction of the second synchronous belt, and after the sample aspirating action is completed, the sampling needle holder block breaks away from the guide track holder block, and then drives the sampling needle to convey the sample in the horizontal direction.

A third objective of the present invention is to provide an auto biochemical analyzer, comprising a sample transport device, wherein the sample transport device comprises a sampling component and a vertical motion system. The sampling component comprises a sampling needle holder block and a sampling needle, and the vertical motion system comprises a second stepping motor and a guide track holder block, the second stepping motor and the sampling component being separately arranged. The sampling needle holder block comprises a guiding column, and the guide track holder block is provided with a hole matched with the guiding column at a corresponding position, and when the sampling component is in contact with the guide track holder block, the guiding column is received in the hole to keep the close contact between the sampling component and the holder block. As the guiding column is mainly responsible for providing a driving force for propelling the motion of the sampling component, the pressure on the guide track is greatly reduced, which is conducive to preventing the deformation of the guide track.

Further improvement of the above-mentioned technical solution is as follows: the vertical motion system further comprises a second synchronous belt, a first guiding shaft parallel to the second synchronous belt and the guide track holder block capable of sliding on the first guiding shaft, the first guiding shaft being fixedly connected with the second synchronous belt.

Further improvement of the above-mentioned technical solution is as follows: when the sampling component is in contact with the guide track holder block, the sampling needle holder block combines with the guide track holder block through the guiding column and the conical hole, and then the sampling needle holder block, together with the guide track holder block, drives the sampling needle to execute tube puncturing and sample aspirating actions under the drive of the second synchronous belt, and after the sample aspirating action is completed, the sampling needle holder block breaks away from the guide track holder block, and then drives the sampling needle to convey the sample in the horizontal direction.

Further improvement of the above-mentioned technical solution is further comprising a transfer guide track, one end of said transfer guide track being in rigid connection with the guide track holder block, and the other end of the said transfer guide track being fixedly connected with the sampling needle holder block.

Further improvement of the above-mentioned technical solution is as follows: the sampling needle respectively stays at a sampling position, a reaction cell position and a counting cell position, wherein the sampling position is closer to the second stepping motor than the reaction cell position and the counting cell position, so that the moment arm of an acting force of the second stepping motor can be shortened, and the moment of the acting force can be reduced.

A fourth objective of the present invention is to provide an auto biochemical analyzer, comprising a frame, a horizontal motion system, a vertical motion system, a sampling component and a transfer guide track. The horizontal motion system comprises a first stepping motor, and the vertical motion system comprises a second stepping motor. The first stepping motor and the second stepping motor are fixedly installed on the frame respectively. The sampling component comprises a sampling needle holder block and a sampling needle. The second stepping motor and the sampling component are separately arranged. The sampling needle holder block comprises a guiding column, and the guide track holder block is provided with a hole matched with the guiding column at a corresponding position. When the sampling component is in contact with the guide track holder block, the guiding column is received in the hole to keep the close contact between the sampling component and the holder block.

Further improvement of the above-mentioned technical solution is as follows: the horizontal motion system further comprises a first synchronous belt and a horizontal guide track; the vertical motion system further comprises a second synchronous belt, a first guiding shaft and the guide track holder block, the guide track holder block being fixedly connected with the second synchronous belt; and the sampling component further comprises a sampling component bracket and a second guiding shaft.

Further improvement of the above-mentioned technical solution is as follows: the sampling component bracket is fixedly connected with the first synchronous belt, and the sampling component bracket is fixed to a sliding block of the horizontal guide track; under the drive of the first stepping motor, the sampling component moves in the horizontal direction under the guide of the horizontal guide track; and the sliding block of the transfer guide track is fixedly connected with the sampling needle holder block, and the sampling needle holder block moves in the vertical direction with the transfer guide track under the drive of the second stepping motor.

Further improvement of the above-mentioned technical solution is as follows: the guide track holder block is fixedly connected with the transfer guide track.

Further improvement of the above-mentioned technical solution is as follows: the sampling needle holder block comprises a guiding column, and the guide track holder block is provided with a hole matched with the guiding column.

Further improvement of the above-mentioned technical solution is as follows: the guiding column is a partial cone.

Further improvement of the above-mentioned technical solution is further comprising an optocoupler switch, which is installed on the frame.

Further improvement of the above-mentioned technical solution is as follows: optocoupler switch sensor chips are respectively installed on the sampling component bracket and the guide track holder block.

Further improvement of the above-mentioned technical solution is as follows: the transfer guide track and the horizontal guide track are parallel to each other.

Further improvement of the above-mentioned technical solution is as follows: the sampling component sequentially moves to a sampling position, a reaction cell position and a counting cell position in the horizontal direction.

The beneficial effects of the present invention are as follows: one end of the transfer guide track is fixed to the guide track holder block, the guide track holder block is provided with a groove matched with the transfer guide track, and meanwhile screws are arranged on the back and the top to ensure the rigid connection. The second sliding block of the transfer guide track is fixed to the sampling needle holder block by a screw, and when the synchronous belts drive the guide track holder block and the transfer guide track to move in the vertical direction, the sampling needle moves up and down accordingly. Optocouplers can be arranged in the horizontal direction and the vertical direction for locating so as to perform sampling and conveying the sample at the specific position. The sampling needle holder block is connected with the guiding column by threads, and the guide track holder block is also provided with the conical hole matched with the guiding column at the corresponding position; in order to reduce the moment necessary during tube puncture, the sampling component moves into contact with the guide track holder block in the horizontal direction, and the sampling needle accomplishes the puncturing action together with the transfer guide track. The motion mechanism and the stepping motors are all fixed to the instrument frame, thereby being smart in motion, compact in space, with the function of conveying the sample to the specified position, low in loading moment require-

DETAILED DESCRIPTION OF THE EMBODIMENTS

Example 1

Figure 1:
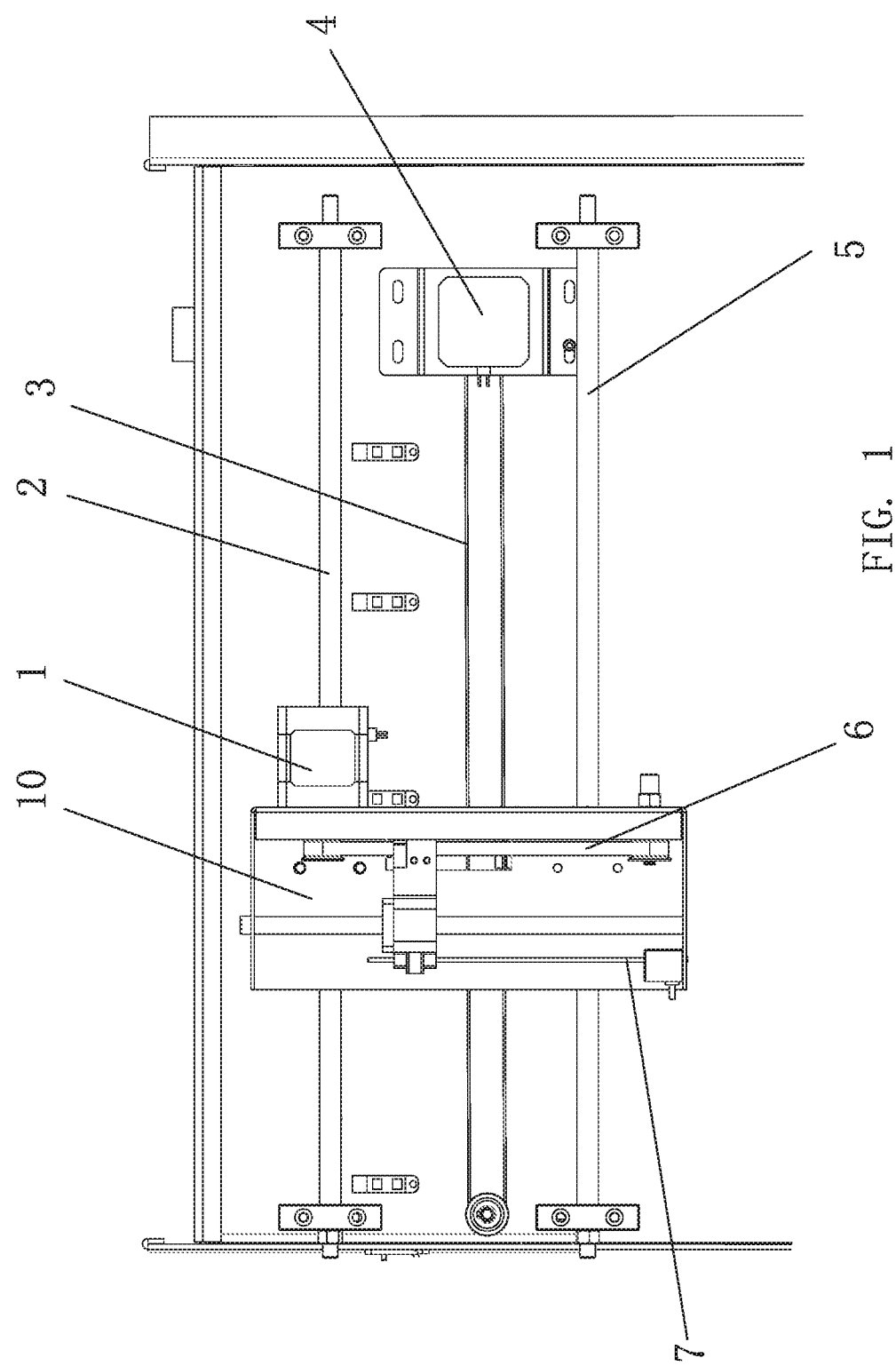
FIG. 1 is a planar schematic diagram of a two-dimensional freedom degree motion mechanism of the present invention.
Figure 2:
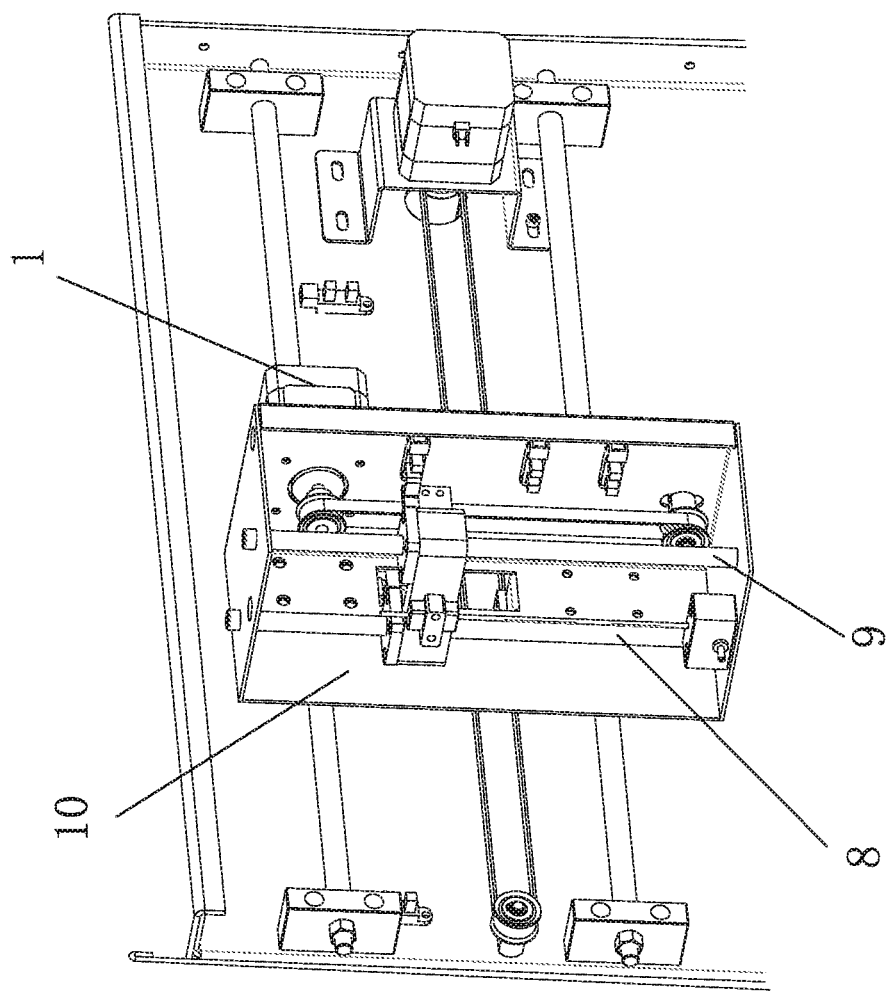
FIG. 2 is a stereoscopic schematic diagram of a two-dimensional freedom degree motion mechanism of the present invention.

Referring to FIGS. 1 and 2, a specific embodiment of a sampling device of the present invention is illustrated. The sampling device uses two horizontal guiding shafts 2 and 5 for guiding. A first stepping motor 4 drives a synchronous belt 3 to cause a sampling component to move in the horizontal direction (the sampling component is fixedly connected with the synchronous belt 3 by a sampling component bracket 10). A second stepping motor 1 installed on the sampling component bracket 10 drives a synchronous belt 6 to drive a sampling needle 7 to move in the vertical direction under the guide of two vertical guiding shafts 8 and 9. The two-dimensional freedom degree motion of the sampling needle 7 in the horizontal direction and the vertical direction is conducive to achieving the functions of tube puncturing, sample aspirating, sample conveying and the like in a hematology analyzer device.

Example 2

FIGS. 3 to 10 show another sampling device having a two-dimensional freedom degree motion mechanism of the present invention. The two-dimensional freedom degree means that the motion mechanism or components therein can respectively move along the directions where two sides of a certain fixed or unfixed included angle are located. The said fixed included angle can be 150 degrees, 120 degrees, 90 degrees, 60 degrees, 30 degrees or any other suitable angle. The movement trajectory of the two-dimensional freedom degree can be a straight line, a smooth curve, a smooth parabola, a broken line or a combination thereof. In a preferred embodiment of the present invention, the two-dimensional freedom degree refers to two straight line directions which are vertical to each other. In a more preferred embodiment, the said two-dimensional freedom degree motion comprises a motion part in the horizontal direction and a motion part in the vertical direction. Specific embodiments of the present invention will be illustrated below by using two-dimensional freedom degree motion in the horizontal direction and the vertical direction as one of the specific embodiments of the present invention. The specific embodiments of two-dimensional freedom degree motions in other angles and in other directions can be obtained by analogy.

Figure 3:
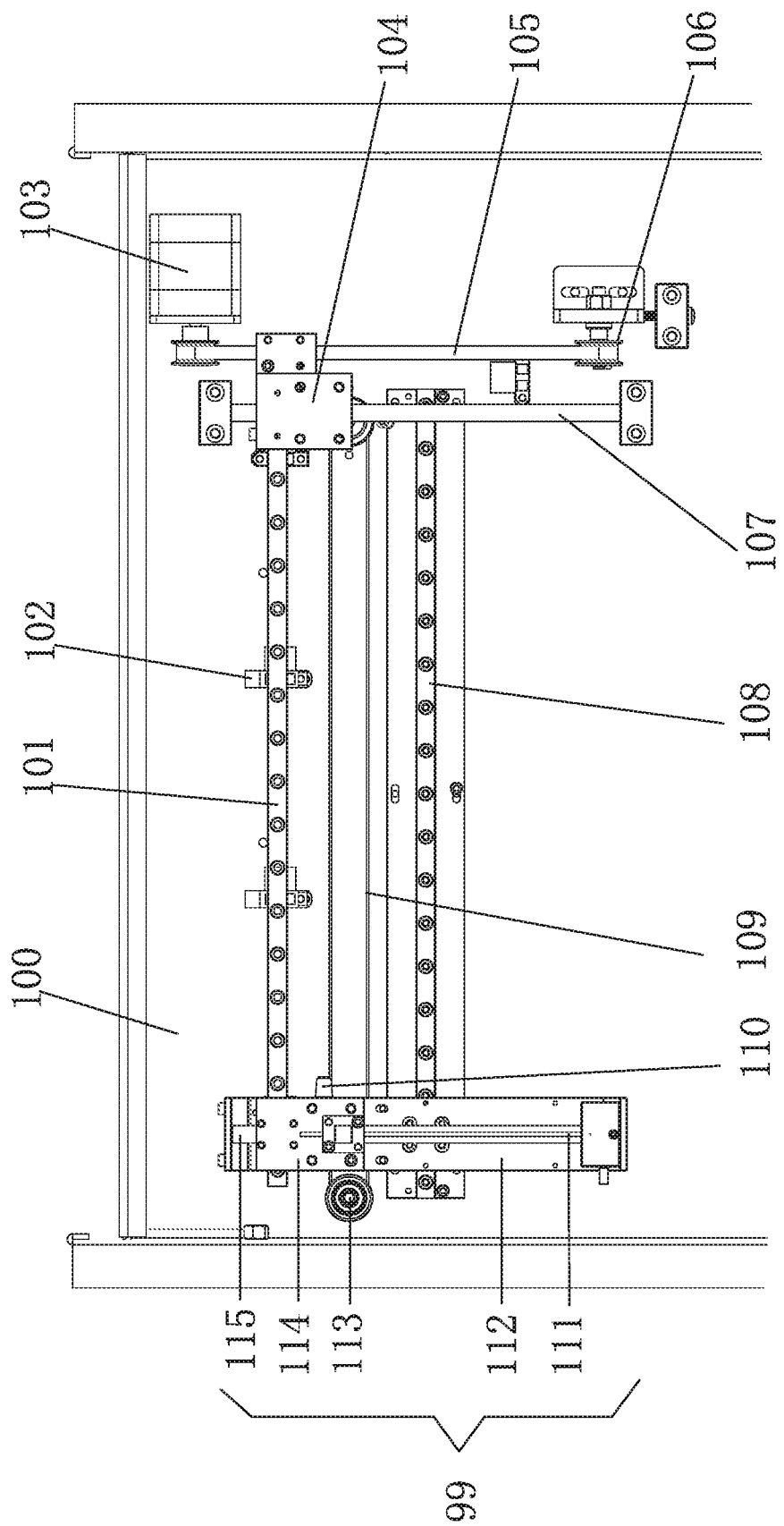
FIG. 3 is a planar schematic diagram of an open sampling position of another two-dimensional freedom degree motion mechanism of the present invention.
Figure 4:
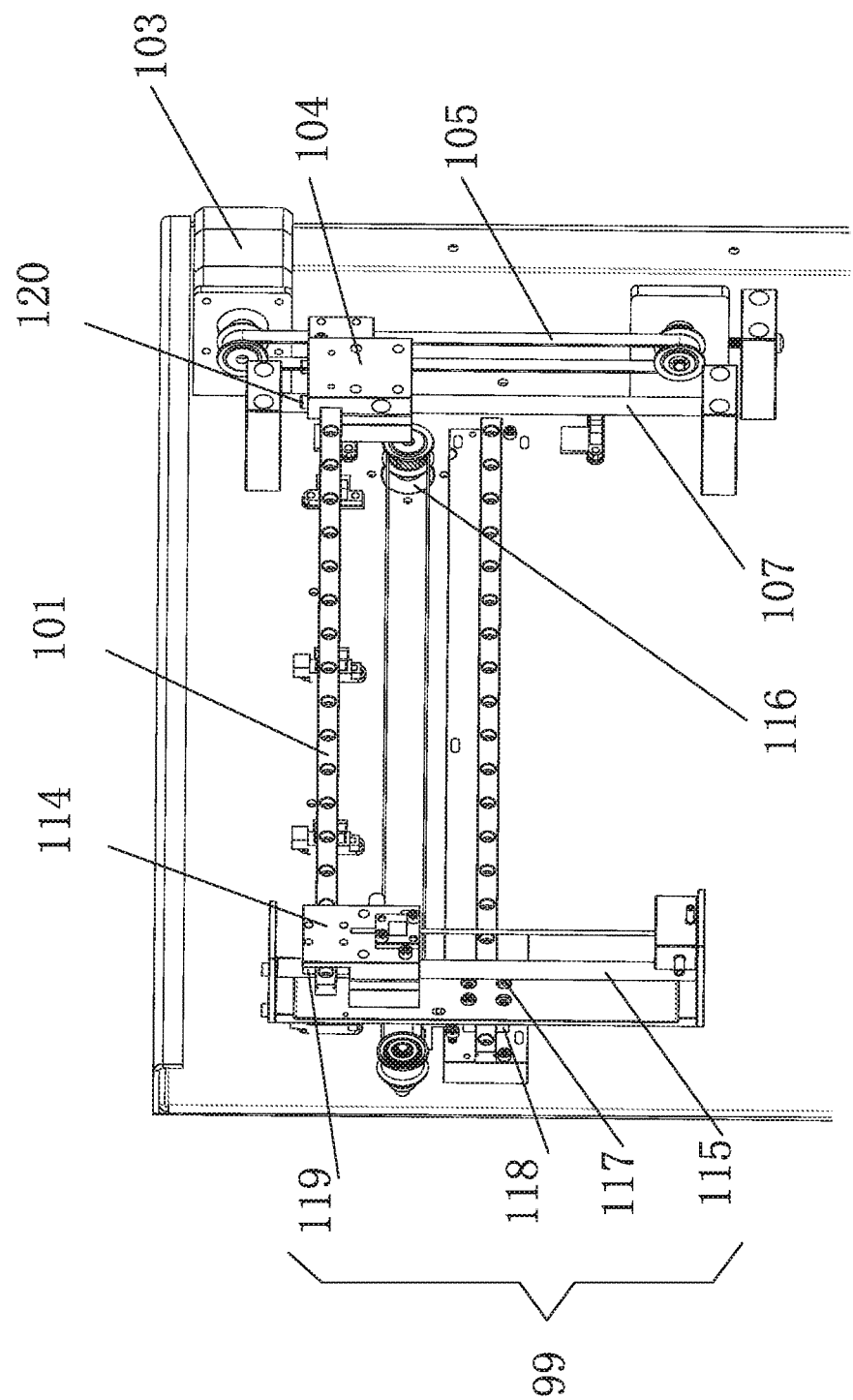
FIG. 4 is a stereoscopic schematic diagram of an open sampling position of another two-dimensional freedom degree motion mechanism of the present invention.
Figure 5:
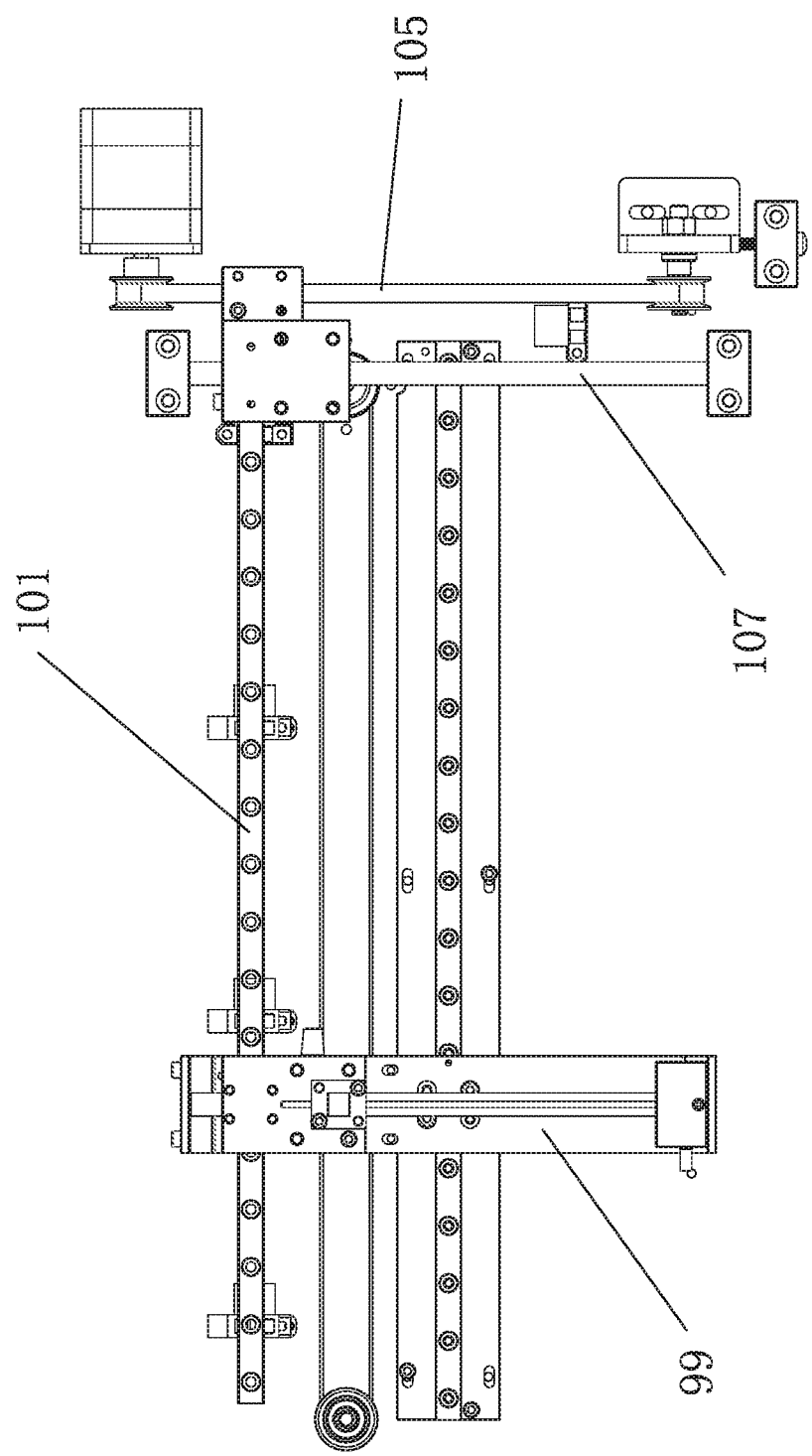
FIG. 5 is a planar schematic diagram when another two-dimensional freedom degree motion mechanism of the present invention moves to a specific position in the horizontal direction.
Figure 6:
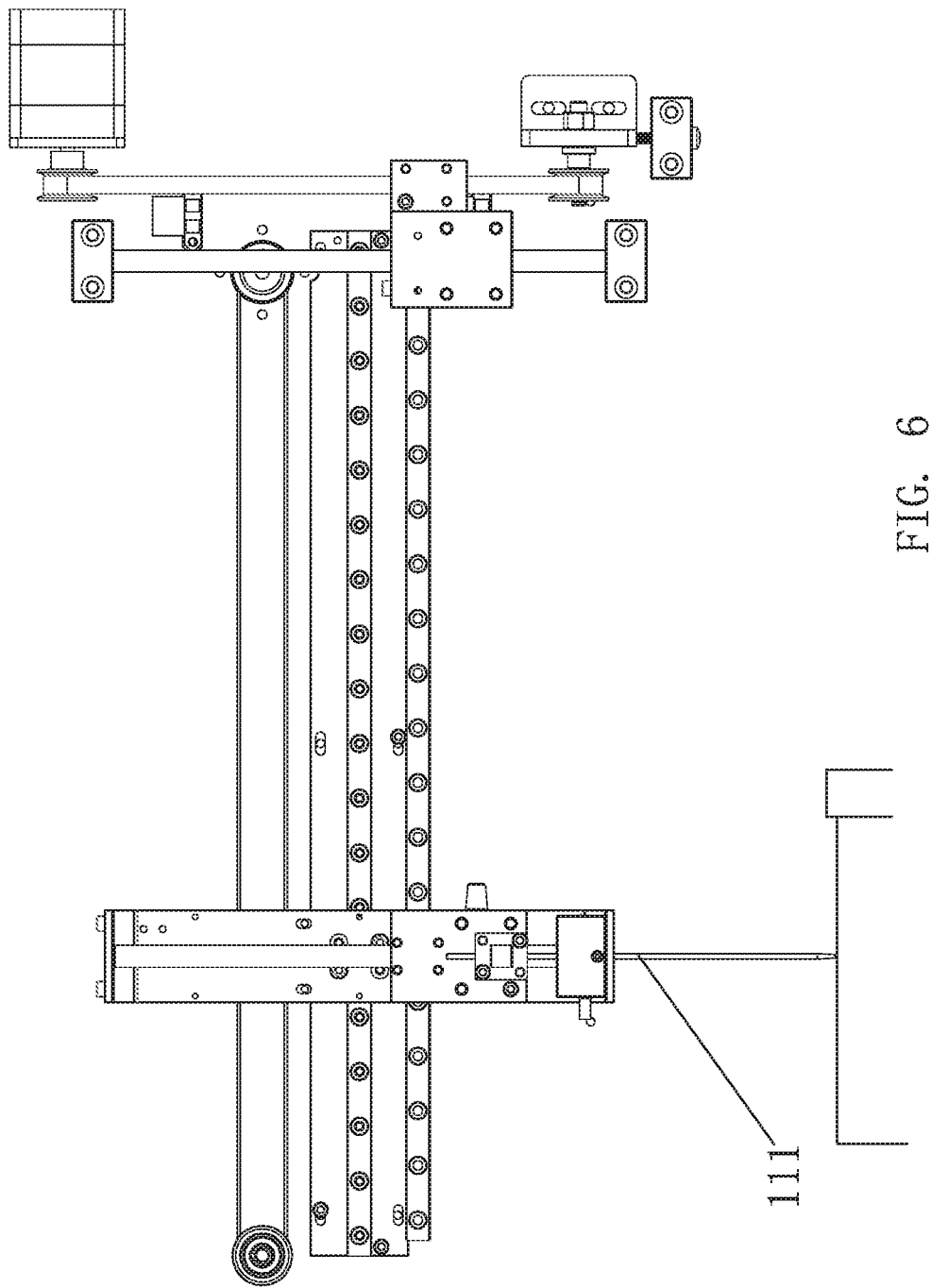
FIG. 6 is a planar schematic diagram when another two-dimensional freedom degree motion mechanism of the present invention moves to another specific position in the vertical direction.
Figure 7:
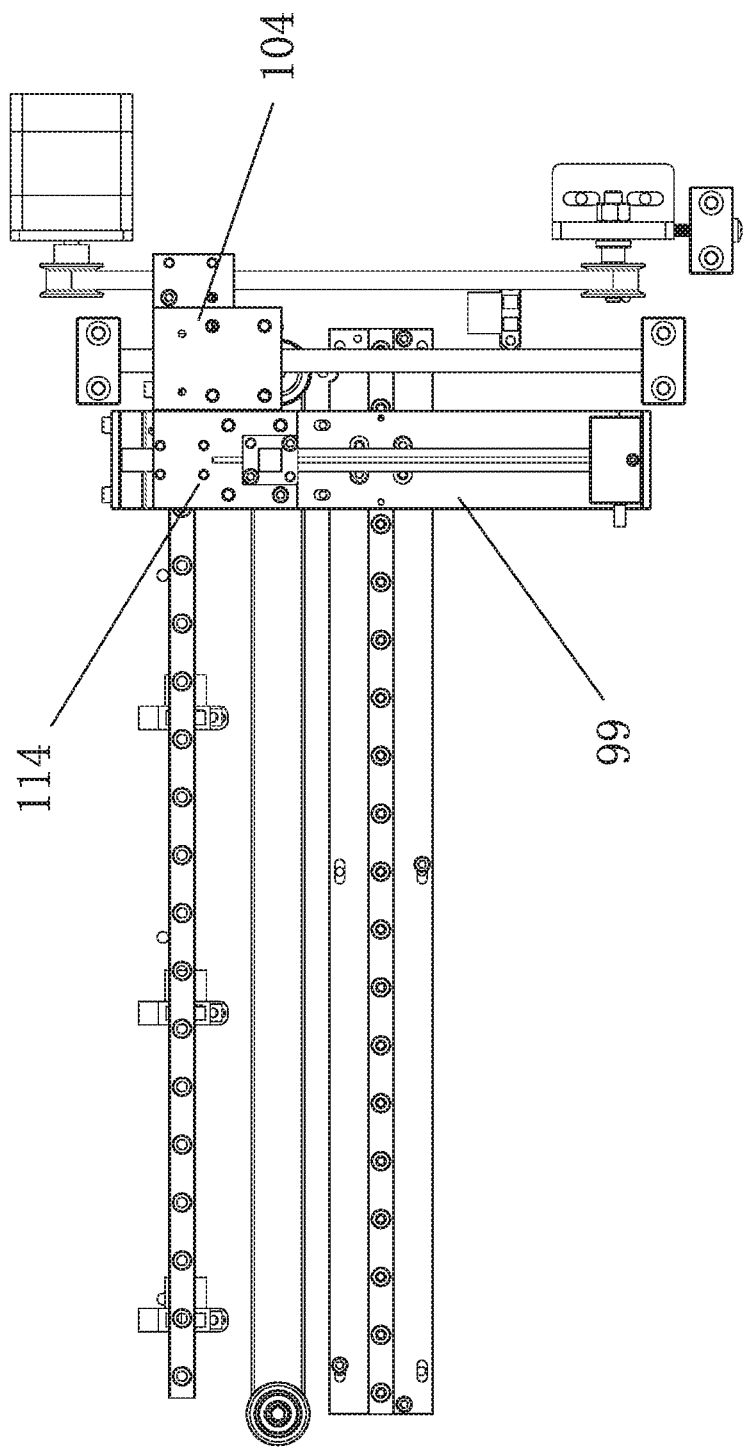
FIG. 7 is a planar schematic diagram when another two-dimensional freedom degree motion mechanism of the present invention moves to a puncturing position in the horizontal direction.
Figure 8:
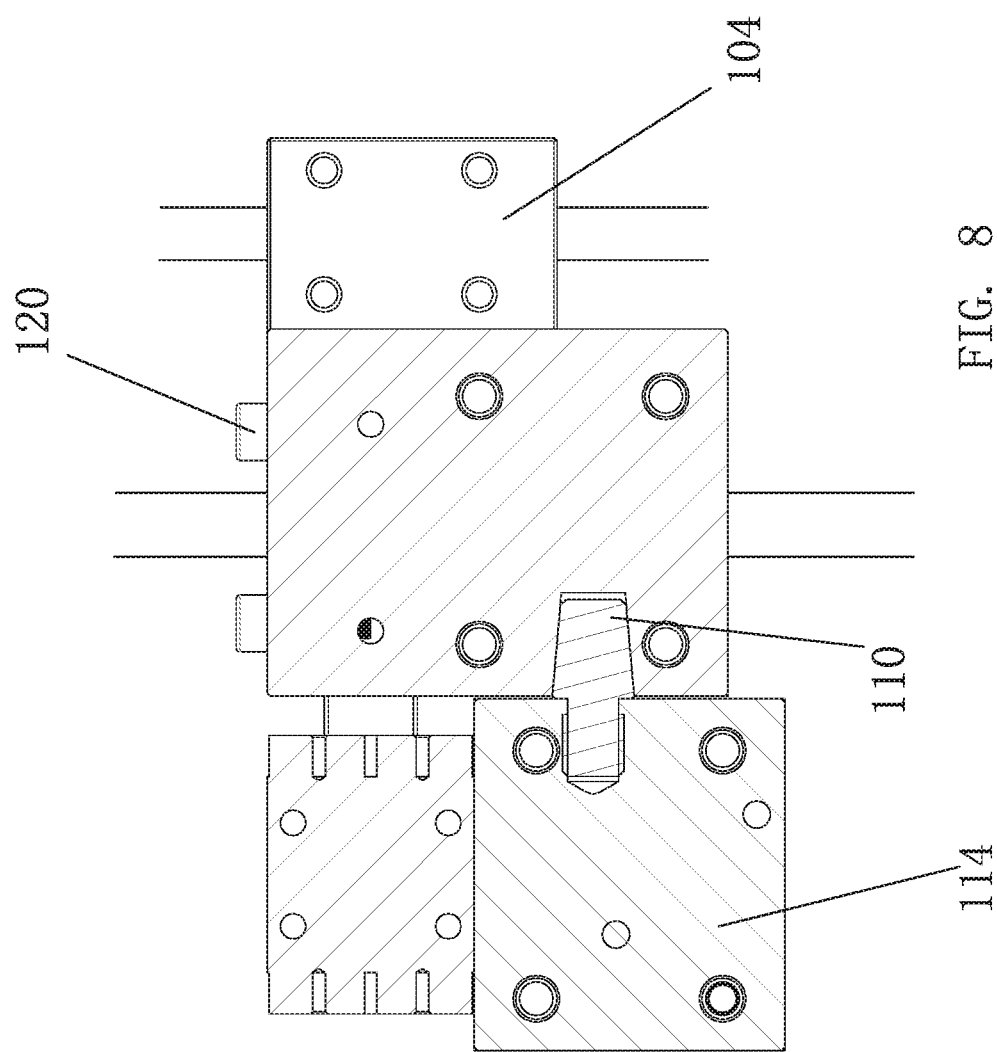
FIG. 8 is a cross-section schematic diagram of a guiding device of another two-dimensional freedom degree motion mechanism of the present invention.
Figure 9:
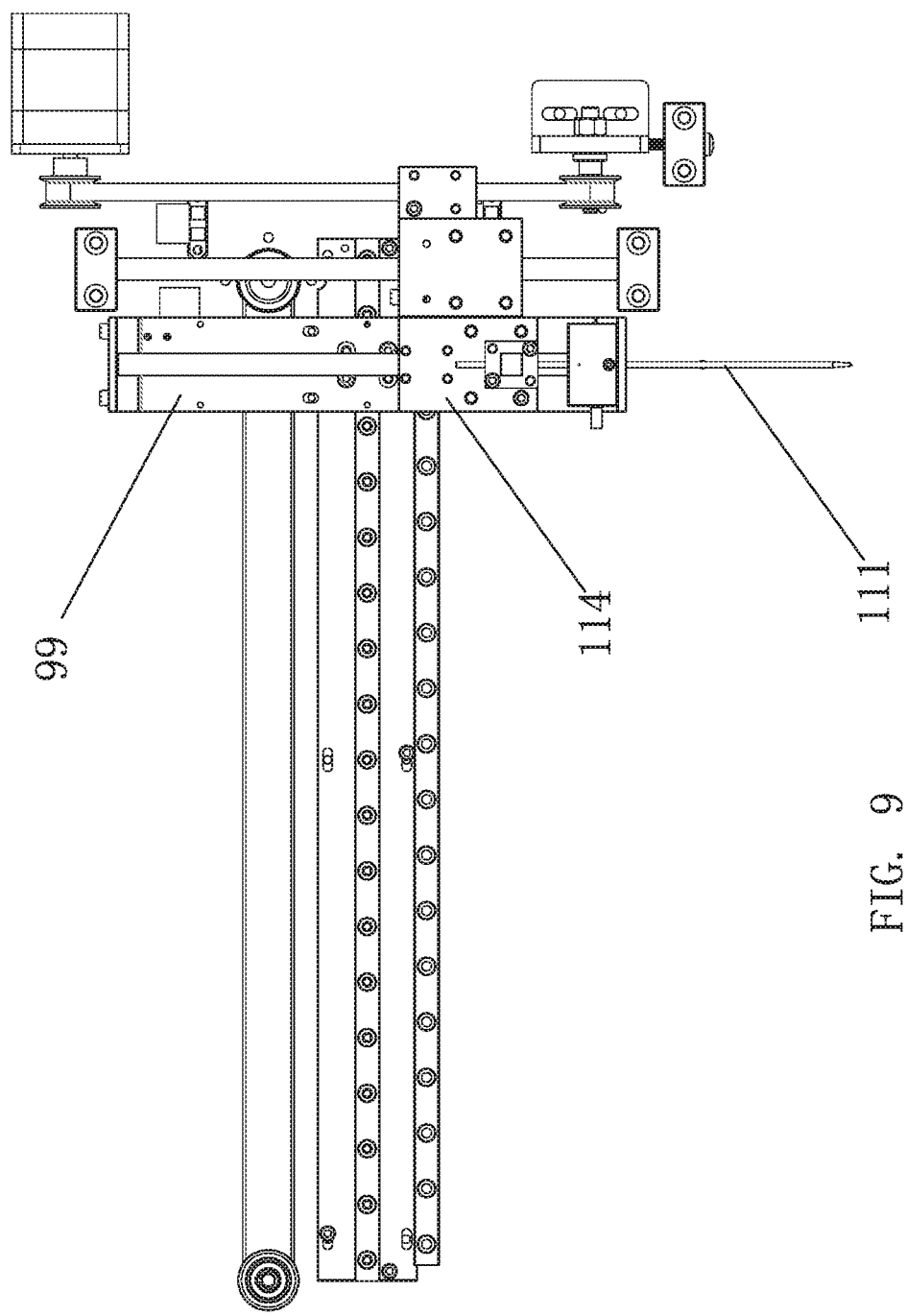
FIG. 9 is a planar schematic diagram of tube puncturing of another two-dimensional freedom degree motion mechanism of the present invention.

Referring to FIGS. 3, 4 and 5, a horizontal motion device comprises a first stepping motor 116 (the main body is shielded and only a rotating shaft is exposed), a first synchronous belt 109, a first synchronous belt wheel 113, a horizontal guide track 108 and a sampling component 99. The said sampling component 99 comprises a sampling component bracket 112, a second guiding shaft 115 fixed to a bracket 112, a sampling needle holder block 114 that is sleeved on the second guiding shaft 115 and can slide along the second guiding shaft 115 in parallel, and a sampling needle 111 fixed to the sampling needle holder block 114, etc. The first stepping motor 116 is fixed to a sampling device frame 100 by a screw, a bolt or a rivet or the like. A rotating shaft of the first stepping motor 116 synchronously rotates with the first synchronous belt wheel 113. The first synchronous belt 109 is installed on the first synchronous belt wheel 113. Preferably, the outer contour of the first synchronous belt wheel 113 is a gear, and the first synchronous belt 109 is a gear belt matched with the gear. The first synchronous belt 109 is driven by the first synchronous belt wheel 113 to move in the horizontal direction. The sampling component bracket 112 is fixed to the first synchronous belt 109 by a screw and a clamping plate (not shown in the figures) and keeps synchronous motion with the first synchronous belt 109. At least one first sliding block 118 is fixed to the sampling component bracket 112. At least one horizontal guide track 108 is fixed to the sampling device frame 100. The first sliding block 118 is in slide fit with the horizontal guide track 108. In a process where the first stepping motor 116 drives the first synchronous belt 109 to move, the first synchronous belt 109 drives the sampling component bracket 112 (together with the entire sampling component 99) to move along the horizontal guide track 108 in the horizontal direction so as to achieve the motion of the device in the horizontal direction.

As shown in FIG. 4, a second sliding block 119 in sliding connection with a transfer guide track 101 is fixedly connected with the sampling needle holder block 114 by a screw. The transfer guide track 101 and the horizontal guide track 108 should be parallel to each other, and therefore, when the first synchronous belt 109 drives the sampling component bracket 112 (together with the entire sampling component 99) to move along the horizontal guide track 108 in the horizontal direction, the sampling needle holder block 114 has no displacement in the vertical direction.

As shown in FIGS. 3 and 4, a vertical motion device comprises a second stepping motor 103, a second synchronous belt 105, a second synchronous belt wheel 106, a guide track holder block 104 and the transfer guide track 101. The second synchronous belt 105 is tensioned by a power output shaft of the second stepping motor 103 and the second synchronous belt wheel 106 and performs synchronous motion with the second stepping motor. Preferably, the second synchronous belt wheel 106 is a gear, and the second synchronous belt 105 is a gear belt matched with the synchronous belt wheel. The transfer guide track 101 is fixed to the second synchronous belt 105 by the guide track holder block 104 and performs synchronous motion with the second synchronous belt 105. The sampling needle holder block 114 is in slide fit with the transfer guide track 101 through the second sliding block 119 thereon, so that the sampling needle holder block can horizontally slide on the transfer guide track 101. The transfer guide track 101, the horizontal guide track 108 and the first synchronous belt 109 are horizontally parallel to each other. A first guiding shaft 107 is fixed to the frame 100, and the guide track holder block 104 is installed on the first guiding shaft 107 and can vertically slide on the first guiding shaft 107. A second guiding shaft 115 is fixed to the sampling component bracket 112, and the sampling needle holder block 114 is installed on the second guiding shaft 115 and can vertically slide on the second guiding shaft 115. The first guiding shaft 107, the second guiding shaft 115 and the second synchronous belt 105 are vertically parallel to each other. When the second stepping motor 103 is started, the second synchronous belt 105 performs synchronous motion with the second stepping motor 103. Since the second synchronous belt 105 is fixedly connected with the guide track holder block 104 and the transfer guide track 101, the transfer guide track 101 is driven by the second stepping motor 103 to move up and down in the vertical direction.

Figure 10:
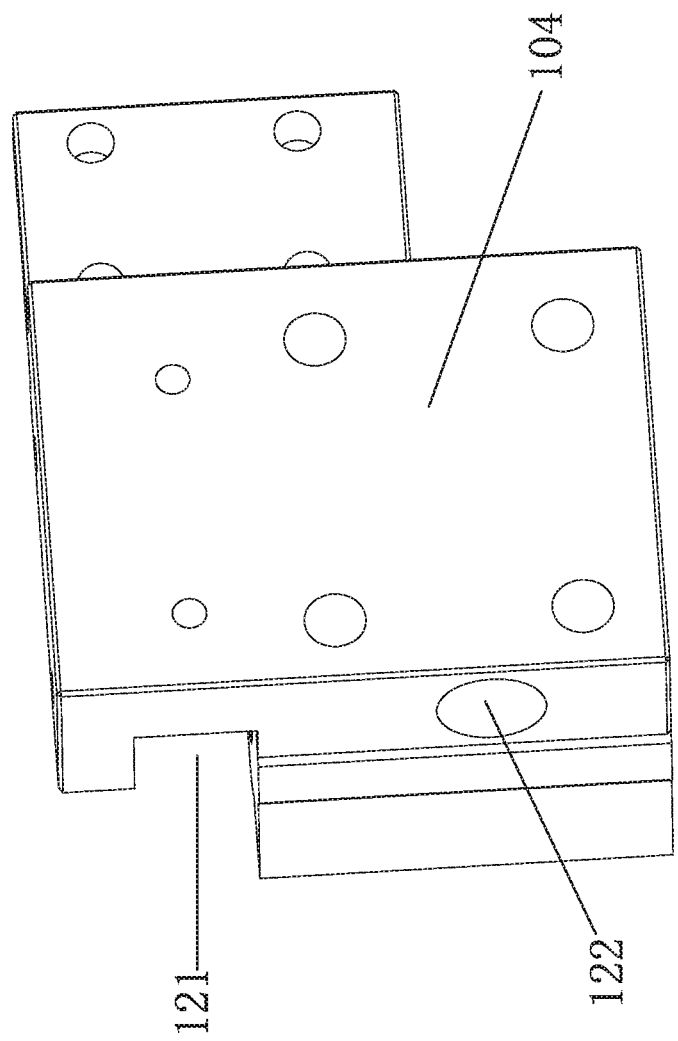
FIG. 10 is a stereoscopic schematic diagram of a structure of another two-dimensional freedom degree motion mechanism of the present invention.

As shown in FIGS. 3 and 4, due to the requirement for guiding, the first guiding shaft 107, the second guiding shaft 115 and the second synchronous belt 105 need to be vertically placed in parallel. The sampling needle holder block 114 and the guide track holder block 104 have linear bearings (not shown in the figures) installed therein and can vertically slide on the second guiding shaft 115 and the first guiding shaft 107 respectively. The guide track holder block 104 fixes the relative positions of the guide track holder block 104 and the second synchronous belt 105 by a screw and a clamping plate (not shown in the figures). The guide track holder block 104 is provided with a groove 121 (as shown in FIG. 10), and the transfer guide track 101 is received in the groove 121, and the guide track holder block 104 is fixedly connected with the transfer guide track 101 by a screw. As mentioned above, the second sliding block 119 in sliding connection with a transfer guide track 101 is fixedly connected with the sampling needle holder block 114, so that the transfer guide track 101 is simultaneously connected with the guide track holder block 104 and the sampling needle holder block 114. The sampling needle holder block 114 and the guide track holder block 104 have the same or similar structures. When the second synchronous belt 105 is driven by the second stepping motor 103 (fixedly installed on the frame) to move in the vertical direction, the guide track holder block 104 indirectly drives, through the transfer guide track 101, the sampling needle holder block 114 to perform reciprocating motion in the vertical direction under the guide of the first guiding shaft 107 and the second guiding shaft 115. As the sampling needle 111 is fixedly connected with the sampling needle holder block 114, the sampling needle 111 can be driven by the second synchronous belt 105 to perform lifting motion in the vertical direction with the transfer guide track 101 so as to accomplish the operations of aspirating a liquid sample and conveying the liquid sample.

In summary, when the second stepping motor 103 does not work and the first stepping motor 116 works, the sampling component 99 can move to a specified position in the horizontal direction, for example, a sampling position, a reaction cell position, a counting cell position or the like. When the first stepping motor 116 does not work and the second stepping motor 103 works, the sampling needle 111 can be driven by the second synchronous belt 105 to perform the lifting motion in the vertical direction with the transfer guide track 101. The accurate locating of the motion in the horizontal and vertical direction and the motion in the vertical direction depends on a plurality of sensing optocouplers 102 installed on the frame 100. The working principle of the optocoupler is as follows: when a sensor chip shields the optocoupler, a switching signal is sent to a control system. Therefore, a steel sensor chip (not shown in the figures) is respectively installed on the sampling component bracket 112 and the guide track holder block 104. Referring to FIG. 10, the guide track holder block 104 is provided with the groove 121 matched with the transfer guide track 101, a screw 120 above the groove tightly abuts against the guide track, and two screws on the front face ensure the reliable connection with the guide track. The surface of the transfer guide track 101 is parallel to the horizontal guide track 108. The transfer guide track 101 has two functions: a. applying horizontal guide to the sampling component; and b. transferring a moment to the sampling component in the vertical direction to perform tube puncturing.

When the liquid sample is aspirated, sometimes the sampling needle needs to puncture a cover of a test tube containing the liquid sample, so certain thrust needs to be applied to the sampling needle. As shown in FIGS. 7 to 10, to achieve an optimal puncturing effect, the sampling component should be close to the guide track holder block 104 as much as possible so as to reduce the moment generated by the transfer guide track 101 as much as possible. To further reduce the pressure on the transfer guide track 101 when the test tube cover is punctured, a guiding column 110 is additionally designed in the present invention. Specifically, a guiding column 110 protrudes from one surface of the sampling needle holder block 114 facing to the transfer guide track 101. The guiding column 110 can be integrally designed with the sampling needle holder block 114 and can also be fixedly connected with the sampling needle holder block 114 by a threaded hole or in other manner. The guiding column 110 can be designed into a cylinder or a cone with a tip portion removed, can also be in any shape with a trapezoidal cross section. The guide track holder block 104 is also provided with a conical hole or a hole 122 in other shape matched with the outline of the guiding column 110 at a corresponding position. When the sampling component is in contact with the guide track holder block 104, the guiding column 110 is inserted in the hole 122 on the holder block 104 and keeps certain close fit. In order to reduce the moment necessary for the tube puncturing, when the sampling component moves into contact with the guide track holder block 104 in the horizontal direction, the sampling needle holder block 114 combines with the guide track holder block 104 mainly through the guiding column 110, and the guide track holder block 104 drives through the guiding column 110 the sampling needle holder block 114 to move downward under the traction of the second synchronous belt 105. The sampling needle holder block 114 further drives the sampling needle 111 to move downward so as to execute actions of puncturing the test tube cover and aspirating the sample. After the sample aspirating, the sampling needle holder block 114 can smoothly break away from the guide track holder block 104 and then drive the sampling needle 111 to convey the sample to the reaction cell position in the horizontal direction.

The sampling device and the sampling method of the present invention have wide applications. For example, they can be applied to the fields of blood cell analyzers and the like.

The foregoing contents are further detailed descriptions of the present invention in conjunction with the specific embodiments, but the specific implementations of the present invention cannot be deemed as being only limited to these illustrations. For those of ordinary skill in the art to which the present invention belongs, multiple simple deductions or replacements (for example, the transfer guide track in the embodiment is a linear ball guide track, which can be changed to a roller type linear slide track or the like) can also be made without departing from the concept of the present invention, and these simple deductions or replacements shall be encompassed within the protection scope of the present invention.

What is claimed is:

1. An auto biochemical analyzer, comprising:
   a sampling device comprising a frame, a horizontal motion system, a vertical motion system, a sampling component and a transfer guide track, wherein
   the horizontal motion system comprises a first stepping motor;
   the vertical motion system comprises a second stepping motor;
   the first stepping motor and the second stepping motor are fixedly installed on the frame respectively;
   the sampling component comprises a sampling needle holder block and a sampling needle;
   the second stepping motor and the sampling component are separately arranged;
   the sampling needle holder block comprises a guiding column protruding from a surface thereof;
   a guide track holder block comprises a hole configured to receive the guiding column at a corresponding position; and
   a control system,
   wherein the control system is configured to cause the horizontal motion system to convey the sampling needle holder block to contact the guide track holder block and thereby insert the guiding column into the hole in the guide track holder block.

2. The auto biochemical analyzer of claim 1, wherein the vertical motion system further comprises
   a second synchronous belt; and
   a first guiding shaft parallel to the second synchronous belt;
   wherein the guide track holder block is fixedly connected with the second synchronous belt and the control system is configured to cause the vertical motion system to convey the guide track holder block along the first guiding shaft under control of the vertical motion system.

3. The auto biochemical analyzer of claim 2, wherein the hen the sampling component control system is configured to cause the vertical motion system to drive the sampling needle downward, aspirate a sample, and to then retract the sampling needle upward when the guiding column is inserted into the hole in the guide track holder block; and to subsequently cause the horizontal motion system to convey the sampling needle holder block away from contact with the guide track holder block.

4. The auto biochemical analyzer of 1, further comprising a transfer guide track, one end of said transfer guide track is in rigid connection with the guide track holder block, and the other end of the transfer guide track is fixedly connected with the sampling needle holder block.

5. The auto biochemical analyzer of claim 1, wherein the control system is configured to cause the sampling needle to be located at each of a sampling position, a reaction cell position and a counting cell position, and wherein the sampling position is closer to the second stepping motor than the reaction cell position and the counting cell position.

* * * * *